United States Patent
Ge et al.

(10) Patent No.: US 12,235,098 B2
(45) Date of Patent: Feb. 25, 2025

(54) METHOD AND DEVICE FOR DETERMINING REASONABLE SAMPLING INTERVAL WITH THREE-DIMENSIONAL (3D) LASER SCANNING, AND STORAGE MEDIUM

(71) Applicant: CHINA UNIVERSITY OF GEOSCIENCES (WUHAN), Wuhan (CN)

(72) Inventors: Yunfeng Ge, Wuhan (CN); Zhongxu Wen, Wuhan (CN); Yitong Hao, Wuhan (CN); Zihao Li, Wuhan (CN); Zilong Zhang, Wuhan (CN); Changyang Liu, Wuhan (CN); Bin Hu, Wuhan (CN); Shiyu Yuan, Wuhan (CN); Zishuo Zhao, Wuhan (CN)

(73) Assignee: CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 0 days.

(21) Appl. No.: 18/885,673

(22) Filed: Sep. 15, 2024

(65) Prior Publication Data
US 2025/0003741 A1  Jan. 2, 2025

(51) Int. Cl.
*G01B 11/30* (2006.01)
*G01N 33/24* (2006.01)

(52) U.S. Cl.
CPC .......... *G01B 11/303* (2013.01); *G01N 33/24* (2013.01)

(58) Field of Classification Search
CPC .............................. G01B 11/303; G01N 33/24
See application file for complete search history.

(56) References Cited

U.S. PATENT DOCUMENTS

| 2003/0184730 A1 | 10/2003 | Price |
| 2008/0219130 A1 | 9/2008 | Salomon et al. |
| 2020/0363202 A1 | 11/2020 | Metzler et al. |

OTHER PUBLICATIONS

"An investigation on the correlation between the joint roughness coefficient (JRC) and joint roughness parameters" Milad Abolfazli, Elsevier, pp. 1-17 (Year: 2020).*

(Continued)

*Primary Examiner* — Michael J Dalbo
*Assistant Examiner* — Kaleria Knox

(57) ABSTRACT

A method for determining a reasonable sampling interval with three-dimensional (3D) laser scanning includes: collecting rock joints; acquiring point cloud data of the rock joints with 3D laser scanning; performing preprocessing on acquired point cloud data; conducting indoor mechanical tests to determine rock mechanics parameters; calculating, with preprocessed point cloud data of the rock joints, joint roughness coefficients (JRCs) under different intervals obtained from statistical roughness parameters; fitting different relational curves according to a scatter plot between the different intervals and the JRCs to obtain a fitting equation; reversely calculating a JRC of the rock joint sample with the rock mechanics parameters to obtain a reversely calculated JRC; and substituting, according to a relational equation between the different intervals and the JRCs, the reversely calculated JRC into the fitting equation to determine a reasonable sampling interval for roughness evaluation.

4 Claims, 10 Drawing Sheets

(56) References Cited

OTHER PUBLICATIONS

"A Description for Rock Joint Roughness Based on Terrestrial Laser Scanner and Image Analysis" Yunfeng Ge1, Huiming Tang1, Scientific Reports, pp. 1-10, May 29, 2015 (Year: 2015).*

"Effect of joint roughness coefficient and size on shear and characteristic strengths of structural planes." Gaojian Hu; Polos Ones, pp. 1-21, Apr. 21, 2022 (Year: 2022).*

* cited by examiner

METHOD AND DEVICE FOR DETERMINING REASONABLE SAMPLING INTERVAL WITH THREE-DIMENSIONAL (3D) LASER SCANNING, AND STORAGE MEDIUM

CROSS-REFERENCE TO RELATED APPLICATIONS

This application claims priority to Chinese Patent Application No. 202410734782.5 with a filing date of Jun. 7, 2024. The content of the aforementioned application, including any intervening amendments thereto, is incorporated herein by reference.

TECHNICAL FIELD

The present disclosure relates to the technical field of rock joints measurement in engineering geological investigation, and in particular to a method and device for determining a reasonable sampling interval with three-dimensional (3D) laser scanning, and a storage medium.

BACKGROUND

Deformation, damage and seepage of rock joints are closely associated with roughness of the rock joints. Due to the rock joints, the rock mass shows obvious non-uniformity, non-continuity, anisotropy and so on. Accurate evaluation on roughness of the rock joints of the unfilled rock mass is considered as a prerequisite to improve an estimation accuracy of a peak shear strength of the rock joints, and is of great significance to slope stability analysis, rock mass stability evaluation, landslide disaster prevention, etc. Hence, how to accurately and quickly acquire geometric information on the rock joints has been a research hotspot in the field of geotechnical engineering and geological engineering.

The geometric information on the rock joints can be acquired by means of contact measurement and non-contact measurement. The contact measurement includes needle outline ruler and simple profile instrument, both of which are applied widely. Because of manual direct measurement, the acquired information on the rock joints is convenient operation, comprehensive and cost-effective. However, this method is defective for a large workload, a long cycle, a low accuracy, etc. For an outcrop located at high and steep cliffs, the contact measurement is achieved hardly, and poses potential safety hazards in severe environments (ice-snow and rainfall). In recent years, with progresses of photoelectric measurement, there emerges a variety of novel non-contact measurement methods, including borehole television, photogrammetry and 3D laser scanning. Particularly, the 3D laser scanning has been used by a large number of scholars in engineering practices. The 3D laser scanning can quickly acquire point cloud data on a surface of a small-sized rock mass, with a high accuracy, and simple scanning. It is simple to build the scanning model of small-size rock joints. However, in an initial processing phase of the point cloud data, the statistical roughness parameter of the rock joints is significantly influenced by a sampling interval. Many scholars worldwide have basically agreed on the influence of the sampling interval on roughness evaluation in their research results. For analysis on a two-dimensional (2D) profile line, a small number of sampling intervals are determined and only four intervals are selected usually, and the emphasis is laid on research on a changing rule of the sampling intervals in the roughness evaluation. Equations for quantizing the roughness parameter with respect to the sampling intervals are not supported and verified by related experiments. To select an optimal sampling interval for roughness evaluation on the laboratory-scale rock joints, there still lacks a more theoretical determination method.

SUMMARY OF PRESENT INVENTION

An objective of the present disclosure is to provide a method and device for determining a reasonable sampling interval with 3D laser scanning, and a storage medium, to solve the technical problem of inaccurate evaluation on roughness of rock joints due to a poor sampling interval at present.

The present disclosure provides a method for determining a reasonable sampling interval with 3D laser scanning, specifically including the following steps:

step S1, collecting rock joint samples;

step S2, acquiring point cloud data of the rock joint samples with 3D laser scanning;

step S3, preprocessing the acquired point cloud data to obtain preprocessed data;

step S4, conducting indoor mechanical tests on the rock joints to determine rock mechanics parameters;

step S5, calculating, with the preprocessed data, joint roughness coefficients (JRCs) under different intervals obtained from statistical roughness parameters;

step S6, fitting different relational curves according to a scatter plot between the different intervals and the JRCs to obtain a fitting equation;

step S7, reversely calculating a JRC of the rock joint samples with the rock mechanics parameters to obtain a reversely calculated JRC;

step S8, substituting, according to a relational equation between the different intervals and the JRCs in the step S6, the reversely calculated JRC in the step S7 into the fitting equation to determine a reasonable sampling interval for roughness evaluation.

The present disclosure provides a storage medium, where the storage medium stores an instruction and data to realize the method for determining a reasonable sampling interval with 3D laser scanning.

The present disclosure provides a device for determining a reasonable sampling interval with 3D laser scanning, including a processor and a storage medium, where the processor is configured to load and execute an instruction and data in the storage medium to realize the method for determining a reasonable sampling interval with 3D laser scanning.

The present disclosure has the following beneficial effects: Based on the reversely calculated JRC for the rock joints, the present disclosure determines the reasonable sampling interval for the point cloud data in the 3D laser scanning, and provides a general form of the fitting equation for determining the sampling interval. This reduces an error in roughness evaluation on the rock joints, and further determines, according to a range of the sampling interval, a range of the reasonable sampling interval for the rock joint samples in the region, thereby facilitating subsequent further applications of the roughness.

DETAILED DESCRIPTION OF THE EMBODIMENTS

In order to make the objective, technical solution and advantages of the present disclosure clearer, implementations of the present disclosure will be further described in detail in conjunction with the accompanying drawings.

Figure 1:
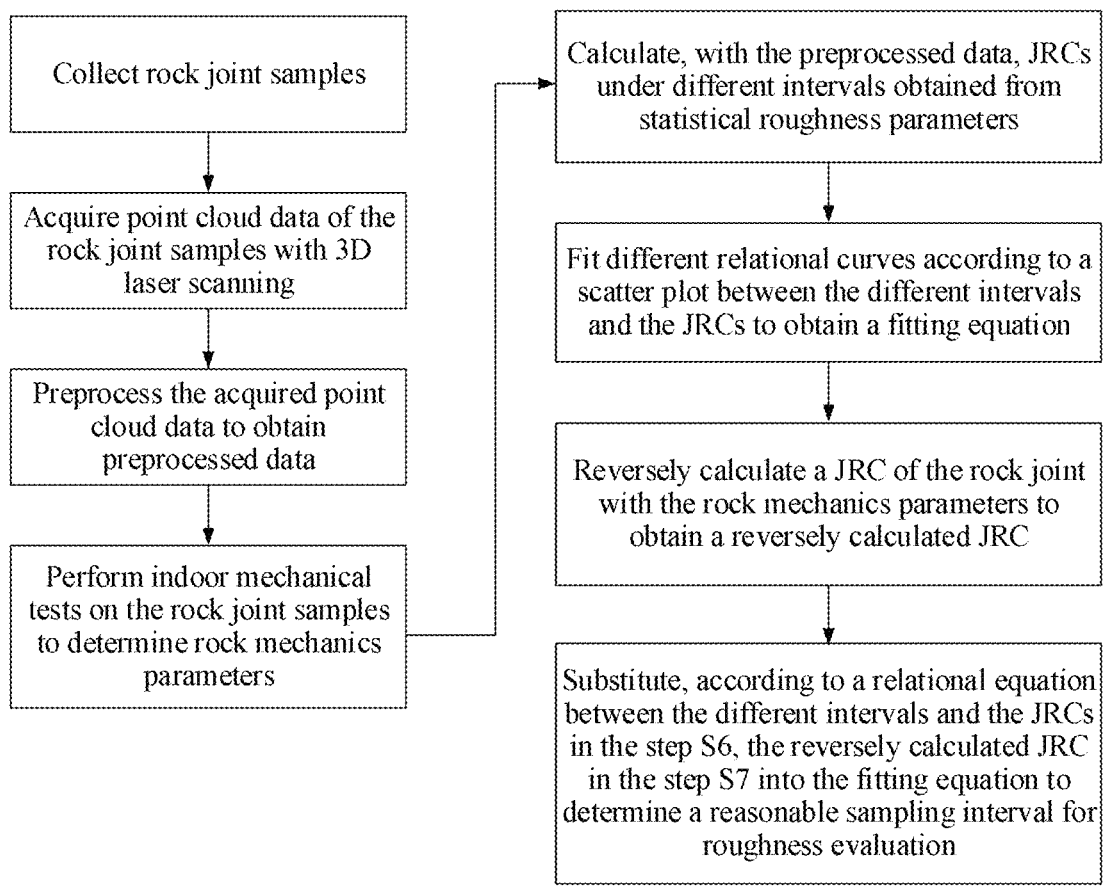
FIG. 1 is a flowchart of a method according to the present disclosure.

Referring to FIG. 1, FIG. 1 is a flowchart of a method according to the present disclosure. The present disclosure provides a method for determining a reasonable sampling interval with 3D laser scanning, specifically including the following steps:

In step S1, rock joint samples are collected.

In step S2, point cloud data of the rock joint samples is acquired with 3D laser scanning.

As an embodiment, an indoor small-sized rock joint is used as an example for description.

In the laboratory, according to a size of a shear box, the field-collected rock sample is cut into a standard sample with a size of about 100 mm×100 mm×50 mm. For ease of a subsequent direct shear test, the upper and lower surfaces of rock joints and the shear direction of the collected rock samples are labeled.

Under an appropriate temperature and an appropriate humidity, an indoor handheld 3D laser scanning test is conducted. According to a size, a color and other information of the rock joints, an appropriate scanning background and an appropriate scanning interval are selected to ensure the accuracy.

In the embodiment of the present disclosure, the sampling resolution is set as 0.1 mm. Other sampling intervals are obtained by downsampling from the 0.1 mm resolution.

Results in 3D laser scanning on the rock joints are shown in Table 1. The scanning range refers to the surface of the rock joints, with a size of about 100 mm×100 mm. Each point cloud on the rock joint includes about 1,500,000 points, and the average point density is about 147 points/mm².

TABLE 1

Information on point cloud data of the rock joint samples

| Serial number | Scanning resolution/mm | Scanning range/mm × mm | Number of points/points | Point density (points/mm²) |
|---|---|---|---|---|
| Sample 1 | 0.1 | 99.9 × 101 | 1447465 | 143 |
| Sample 2 | 0.1 | 101 × 101 | 1511850 | 149 |
| Sample 3 | 0.1 | 101 × 99.6 | 1756188 | 175 |

In step S3, the acquired point cloud data is preprocessed to obtain preprocessed data.

It is to be noted that the preprocessing in the present disclosure includes point cloud data filtering and point cloud data denoising.

Specifically, the preprocessing includes: Point cloud data out of a research surface is deleted, and only point cloud data at a top of the scanned rock joint is retained. The rock joints are adjusted to a same shearing direction, for ease of subsequent calculation.

In addition, downsampling is performed on point cloud data for each rock joint to generate a series of point cloud data at different sampling intervals in the present disclosure. The sampling intervals are within a sparse range of 0.1 mm to 5 mm, and have a stride of 0.1 mm. Hence, each rock joint sample can be divided into 50 samples at different sampling intervals. Meanwhile, for fear of a size effect, the research region selected in the present disclosure is a 90 mm×90 mm effective data portion.

In step S4, indoor mechanical tests are conducted on the rock joint samples to determine rock mechanics parameters.

It is to be noted that the indoor mechanics test in the step S4 includes a direct shear test, a tilt test and a uniaxial compression test.

As a specific embodiment, the three tests have the following process:

1) Direct shear test on the rock joints: The direct shear test is conducted on the rock joints under different normal loads, thereby obtaining mechanics parameters for the rock joints.

2) Tilt test on the rock joints: When a tilt test platform is used, the upper and the lower for each rock joint are placed sequentially. As the platform rotates and tilts, the upper rock joint surface begins to slide once it reaches the corresponding angle. The rotation angle at this moment is recorded as the basic friction angle for this set of experiments. In view of an operational error in the test, the tilt test is conducted on each rock joint for 5 times, and a median is used, thereby obtaining a basic frictional angle for each rock joint sample. When the test is repeated, a contact surface of the rock joint surface is cleaned, so as to reduce an error in each test.

3) Uniaxial compression test: A joint compressive strength (JCS) for the rock joint is determined through the uniaxial compression test.

Upon completion of the test, the rock mechanics parameters include a normal stress $\sigma$, a peak shear strength $\tau_p$, the basic frictional angle $\varphi_b$, and the joint compressive strength JCS.

Referring to Table 2, Table 2 is a summary of results in the indoor mechanics test.

TABLE 2

| | Results in the indoor mechanical tests | | | |
|---|---|---|---|---|
| Serial number | Peak shear strength $\tau_p$/MPa | Normal stress $\sigma$/MPa | JCS/MPa | Basic frictional angle $\varphi_b$/° |
| Sample 1 | 0.891 | 0.990 | 30.0 | 33.6 |
| Sample 2 | 1.933 | 2.466 | 30.0 | 35.5 |
| Sample 3 | 0.508 | 0.498 | 91.0 | 23.0 |

In step S5, with the preprocessed data, JRCs (which are used to describe roughness of rock fractures or fractures in a rock-soil body) are calculated under different intervals obtained from statistical roughness parameters.

As an embodiment, along the shearing direction of the rock joints, a series of 2D profiles are extracted in a point cloud model (an interval of the 2D profiles selected is the same as a sampling interval of a point cloud for the rock joint sample) to calculate a roughness parameter of each 2D profile.

The JRC is widely used to evaluate the roughness of the rock joints in engineering practices. With simple calculation and good reliability, the JRC is used as a standard roughness evaluation method.

Since a deviation of inclination angle $SD_i$ is strongly associated with the JRC, the step S5 specifically includes:

In step S51, roughness on the rock joint is evaluated with a roughness parameter $SD_i$ by:

$$SD_i = \tan^{-1}\sqrt{\frac{1}{L}\sum_{j=1}^{N-1}\left(\frac{z_{j+1}-z_j}{y_{j+1}-y_j}-\tan i_{ave}\right)^2 (y_{j+1}-y_j)}$$

$$i_{ave} = \tan^{-1}\left(\frac{1}{L}\sum_{j=1}^{N-1}|z_{j+1}-z_j|\right)$$

wherein, $z_{j+1}$ and $z_j$ are respectively a Z-coordinate of a (j+1)th point and a Z-coordinate of a jth point in a given 2D profile, $y_{j+1}$ and $y_j$ are respectively a Y-coordinate of the (j+1)th point and a Y-coordinate of the jth point, N is a total number of points in any 2D profile of the rock joints, L is a profile length, and $i_{ave}$ is an average dip angle.

In step S52, a $JRC^{2D}$ of a single 2D profile is calculated according to the roughness parameter $SD_i$.

In step S53, JRCs of all 2D profiles of the rock joint are averaged to determine a $JRC^{3D}$ of the whole rock joint:

$$JRC^{2D} = 1.14SD_i - 3.88$$

$$JRC^{3D} = \frac{1}{M}\sum_{k=1}^{M}JRC_k^{2D}$$

wherein, M is a total number of the 2D profiles of the rock joint, and i is an ith 2D profile.

In step S54, the scatter plot between the sampling intervals and the JRCs is drawn.

In step S6, different relational curves are fitted according to the scatter plot between the different intervals and the JRCs to obtain a fitting equation.

As an embodiment, the step S6 specifically includes:

In step S61, the relational curves between the sampling intervals and the JRCs include the first exponential type, the second exponential type and a Logistic type.

Figure 2:
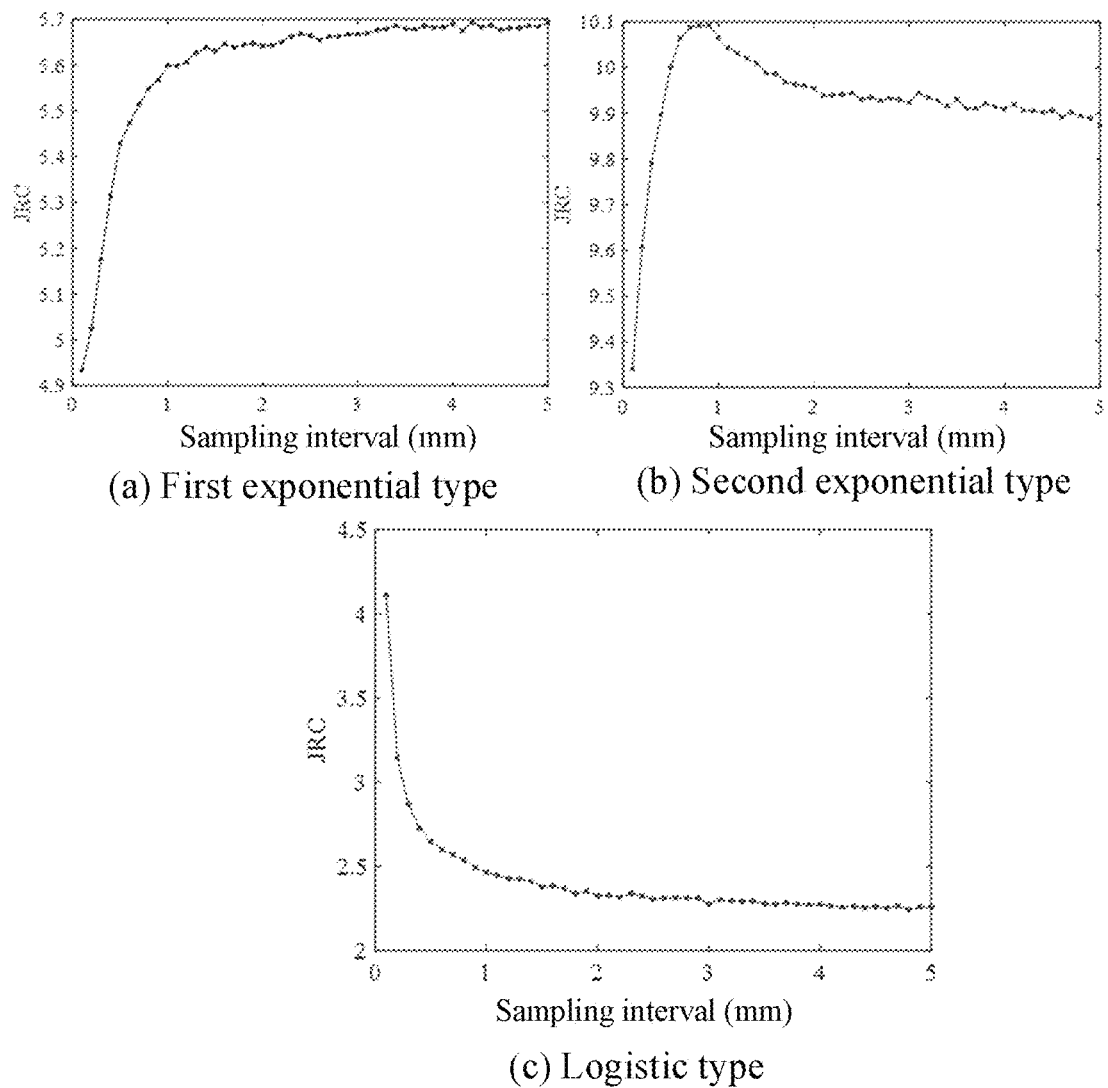
FIG. 2 is a schematic diagram of a first exponential type curve, a second exponential type curve and a Logistic type curve.

The JRCs calculated with the $SD_i$ under different intervals are determined. The relational graph between the JRCs and the sampling intervals is drawn. As shown in FIG. 2, a relation between the JRCs and the sampling intervals mainly includes an exponential type and a Logistic type.

Both the exponential type and the Logistic type infinitely approach to a constant. The exponential type may include the first exponential type and the second exponential type.

Referring to FIG. 2, the first exponential type refers to that a curve rises and then directly approaches to a constant. The second exponential type includes a growth phase and an attenuation phase (a peak or a valley), where the curve initially increases and then decreases, or initially decreases and then increases, before eventually stabilizing at a constant. The Logistic type refers to that a curve declines first and then approaches to a constant.

In step S62, each of the relational curves is observed. A step S63 is proceeded if the relational curve is the first exponential type. A step S64 is proceeded if the relational curve is the second exponential type. A step S65 is proceeded if the relational curve is the Logistic type.

In step S63, the fitting equation is defined as $y=A_1 \times e^{-x/t_1}+y_0$ or a second order form $y=A_1 \times e^{(-x/t_1)}+A_2 \times e^{(-x/t_2)}+y_0$. In the foregoing equation, $A_1$ is an attenuation coefficient, and controls a rate and a direction in attenuation or growth, $t_1$ is a time scale in the attenuation or the growth and is a constant term, $y_0$ is an offset and a constant term, and determines a position of a curve below or above an x-axis.

It is to be noted that in response to a positive value of the $A_1$, the JRC is negatively correlated with the sampling interval, and as the sampling interval increases, the JRC decreases. In response to a negative value of the $A_1$, the JRC is positively correlated with the sampling interval, and as the sampling interval increases, the JRC increases.

In step S64, fitting is performed by:

$$y = \begin{cases} y_0 + A_d + A_g\left(e^{x_c/t_g} - e^{-x/t_g}\right) & x \leq x_c \\ y_0 + A_d e^{-x-x_c/t_d} & x > x_c \end{cases}$$

wherein, the two stags of the equation are the growth and the attenuation, respectively, and $y_0$, $A_d$, $A_g$, $t_g$, $x_c$, and $t_d$ are undetermined coefficients, which determine a speed and other characteristics in the growth and the attenuation. There may be multiple solutions for the sampling interval. The interval is selected according to an actual condition.

In step S65, fitting is performed by:

$$y = A_2 + (A_1 - A_2)/(1 + (x/x_0)^p)$$

$A_1$: an upper limit of a Logistic function (or a saturation value); as x tends to a positive infinity, the function value y tends to $A_1$;

$A_2$: a lower limit of the Logistic function; when the x approaches to a negative infinity, the functional value y approaches to $A_2$;

p: a shape parameter, which affects steepness of a curve of the Logistic function, and is usually called a slope parameter;

$x_0$: a midpoint parameter of the Logistic function, which is a central position on the curve of the function, and may also be understood as a turning point on the curve of the function.

In step S7, a JRC of the rock joint is reversely calculated with the rock mechanics parameters to obtain a reversely calculated JRC.

It is to be noted that the reversely calculated JRC in the step S7 is specifically given by:

$$\begin{cases} \tau = \sigma \tan\left[\varphi_b + JRC1g\left(\dfrac{JCS}{\sigma}\right)\right] \\ JRC = \dfrac{\arctan(\tau/\sigma) - \varphi_b}{1g(JCS/\sigma)} \end{cases}.$$

wherein, $\tau$ is the peak shear strength of the rock joint obtained in the test.

As an embodiment, in combination with the parameters of the indoor test in Table 2, the JRC of the sample 1, the JRC of the sample 2 and the JRC of the sample 3 are respectively 5.66, 2.39 and 9.98.

In step S8, according to a relational equation between the different intervals and the JRCs in the step S6, the reversely calculated JRC in the step S7 is substituted into the fitting equation to determine a reasonable sampling interval for roughness evaluation.

Specifically, according to the fitting equation, the reasonable sampling interval for a rock joint is determined with the reversely calculated JRC. In the relational curve between the JRCs and the sampling intervals, when the reversely calculated JRC is k, a horizontal coordinate of an intersection between the curve and the straight line is determined as the sampling interval.

Figure 3:
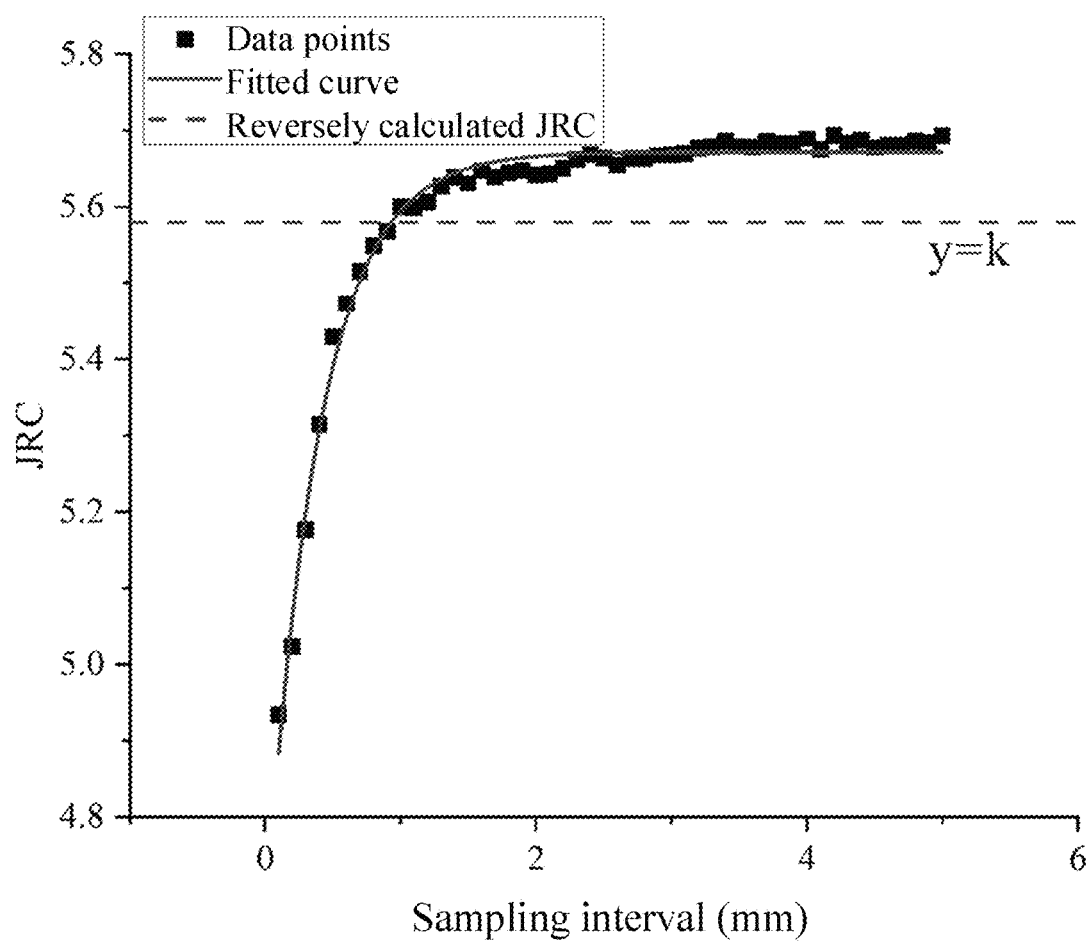
FIG. 3 is a schematic diagram for determining a sampling interval of the first exponential type curve.

Referring to FIG. 3, FIG. 3 is a schematic diagram for determining a sampling interval of the first exponential type curve.

When the curve is the first exponential type, the sampling interval is determined by:

$$\begin{cases} y = k \\ y = A_1 \times e^{-x/t_1} + y_0 \end{cases}.$$

The sampling interval is obtained by:

$$x = -t_1 \times \ln\left(\dfrac{k - y_0}{A_1}\right).$$

When the curve is the second exponential type, the sampling interval is solved by:

$$\begin{cases} e^{-\tfrac{x_c}{t_g}} - e^{-\tfrac{x}{t_g}} = \dfrac{k - y_0 - A_d}{A_g} & (x \le x_c) \\ x = x_c - t_d \ln\left(\dfrac{k - y_0}{A_d}\right) & (x > x_c) \end{cases}.$$

When the curve is the Logistic type, the sampling interval is solved by:

$$x = x_0 \times \left(\dfrac{A_1 - A_2}{k - A_2} - 1\right)^{\tfrac{1}{p}}.$$

It is to be noted that a range of the reasonable sampling interval of the rock joints in the sampling region is determined through the fitting equation. It is to be noted that the fitting equation is an exponential attenuation or growth model or a general form of the Logistic type. For rock joints in different regions, fitting coefficients such as $A_1$, $t_1$ and $y_0$ are different.

As an example, relevant test data in Table 1 and Table 2 are used.

Figure 4:
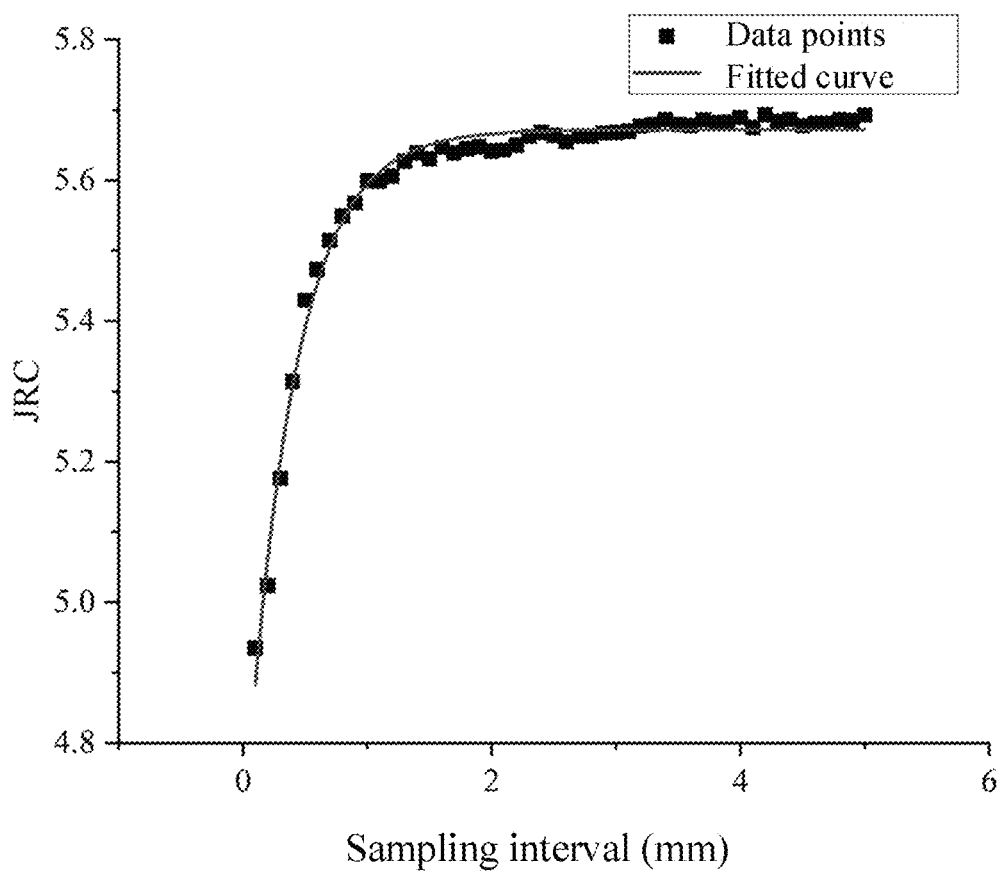
FIG. 4 is a schematic diagram for fitting the first exponential type curve according to an embodiment of the present disclosure.

According to the fitting equation of the sampling interval, for the sample 1, the first exponential type is used for fitting to obtain the curve as shown in FIG. 4:

The equation obtained by the fitting is as follows:

$$y = 5.672 + \left(-0.975 \times e^{-2.474x}\right).$$

Therefore, $A_1 = -0.975$, $1/t_1 = 2.474$ and $y_0 = 5.672$. The fitting coefficients are substituted into the equation of the sampling interval to obtain:

$$x = -\dfrac{1}{2.474} \times \ln\left(\dfrac{k - 5.672}{-0.975}\right).$$

Figure 5:
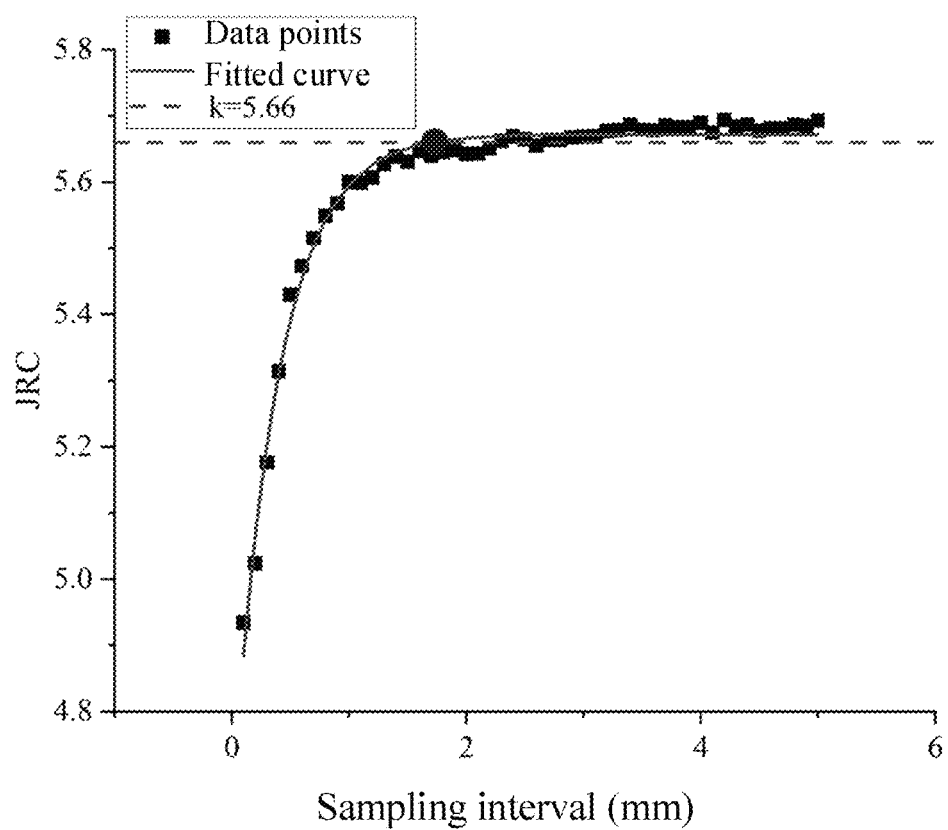
FIG. 5 is a schematic diagram for solving a interval of the first exponential type curve according to an embodiment of the present disclosure.

Further, the reversely calculated JRC is considered as the horizontal line. The horizontal coordinate at the intersection between the horizontal line and the fitted curve is determined as the sampling interval, as shown by the blue intersection point in FIG. 5. By substituting y=k=5.66 into the equation, the sampling interval is 1.77 mm.

Figure 6:
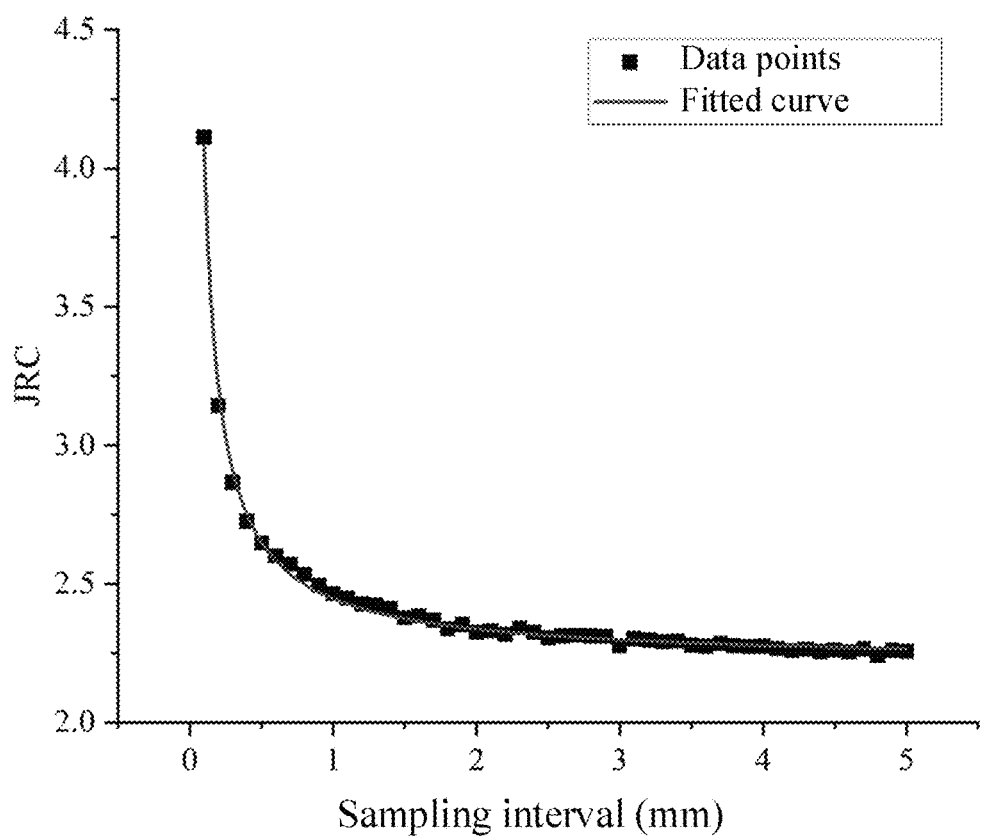
FIG. 6 is a schematic diagram for fitting the Logistic type curve according to an embodiment of the present disclosure.

For the sample 2, the Logistic type is used for fitting to obtain the curve as shown in FIG. 6: The fitting equation is as follows:

$$y = 2.21 + (680.135 - 2.21)/\left(1 + (x/1.422 \times 10^{-4})^{0.899}\right).$$

Therefore, $A_1 = 680.135$, $A_2 = 2.21$ m $p = 0.899$ and $x_0 = 1.422 \times 10^{-4}$. The fitting coefficients are substituted into the equation of the sampling interval to obtain:

$$x = 1.422 \times 10^{-4} \times \left(\dfrac{680.135 - 2.21}{k - 2.21} - 1\right)^{\tfrac{1}{0.899}}.$$

Figure 7:
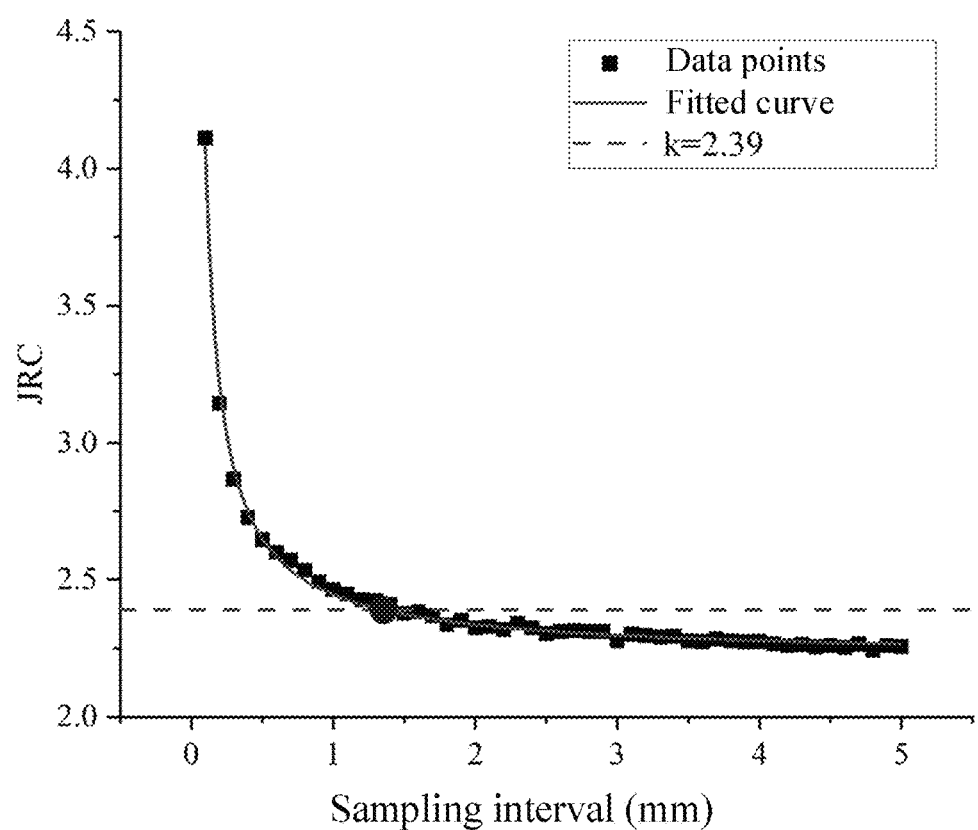
FIG. 7 is a schematic diagram for solving a interval of the Logistic type curve according to an embodiment of the present disclosure.

Likewise, according to the relational graph between the JRC and the fitted curve in FIG. 7, the reversely calculated JRC y=k=2.39 is substituted into the equation, and the sampling interval is 1.35 mm.

For the sample 3, the second exponential type is used for fitting to obtain:

$$y = \begin{cases} 9.901 + 0.208 + 1.227\left(e^{-0.746/0.265} - e^{-x/0.265}\right) & x \le 0.746 \\ 9.901 + 0.208 e^{-(x-0.746)/0.972} & x > 0.746 \end{cases}$$

Figure 8:
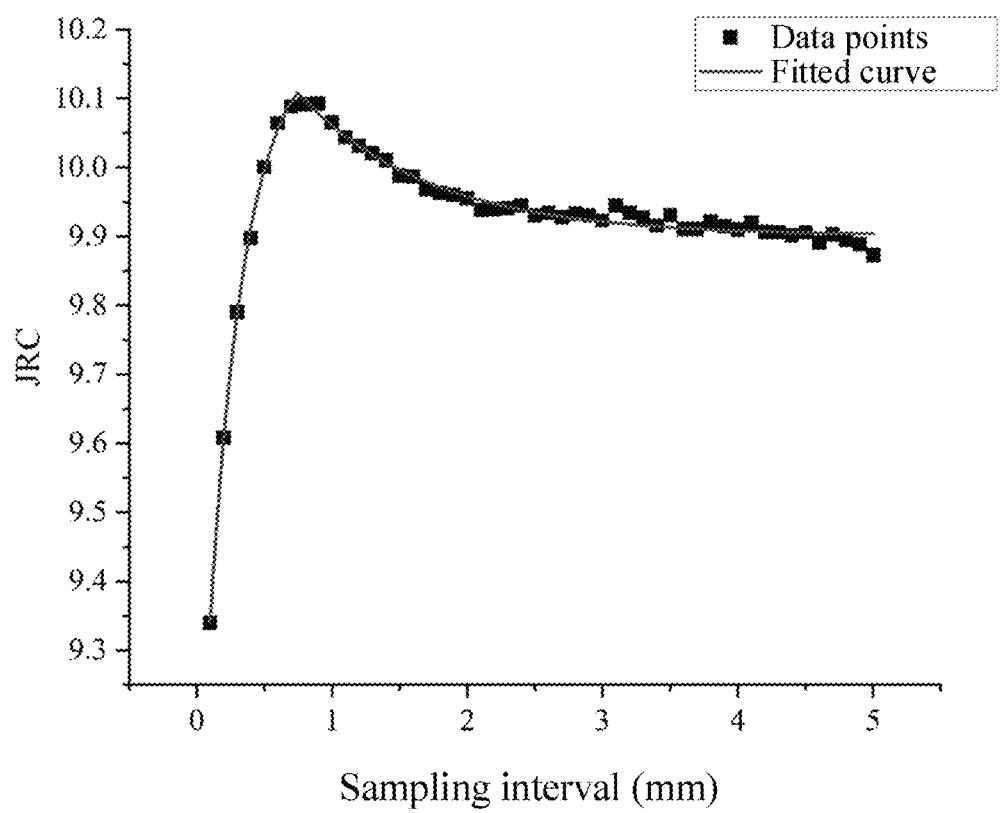
FIG. 8 is a schematic diagram for fitting the second exponential type curve according to an embodiment of the present disclosure.

The curve is as shown in FIG. 8. Therefore, the $y_0$, the $x_c$, the $A_g$, the $t_g$, the $A_d$, and the $t_d$ are respectively 9.901, 0.746, 1.227, 0.265, 0.208, and 0.972. The fitting coefficients are substituted into the equation of the sampling interval to obtain:

$$\begin{cases} e^{-\frac{0.746}{0.265}} - e^{-\frac{x}{0.265}} = \frac{k - 9.901 - 0.208}{1.227}(x \le x_c) \\ x = 0.746 - 0.972\ln\left(\frac{k - 9.901}{0.208}\right)(x > x_c) \end{cases}$$

Figure 9:
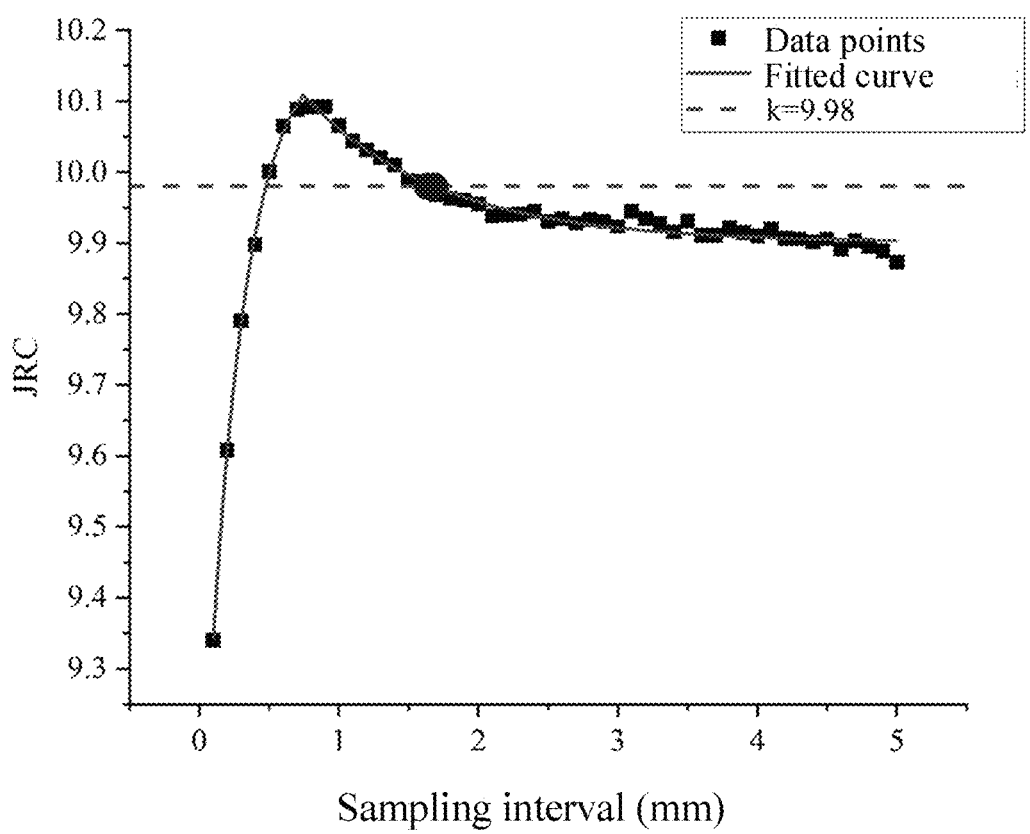
FIG. 9 is a schematic diagram for solving a interval of the second exponential type curve according to an embodiment of the present disclosure.

Likewise, according to the relational graph between the JRC and the fitted curve in FIG. 9, the reversely calculated JRC y=k=9.98 is substituted into the equation, and x=0.75 mm or 1.69 mm. The slope at the second intersection changes little, and the sampling interval is 1.69 mm.

Therefore, for the three samples, the reasonable sampling intervals for the roughness evaluation fall into a range of 1.35-1.77 mm, and the average reasonable sampling interval is 1.6 mm. The more the samples, the more applicable the result.

Figure 10:
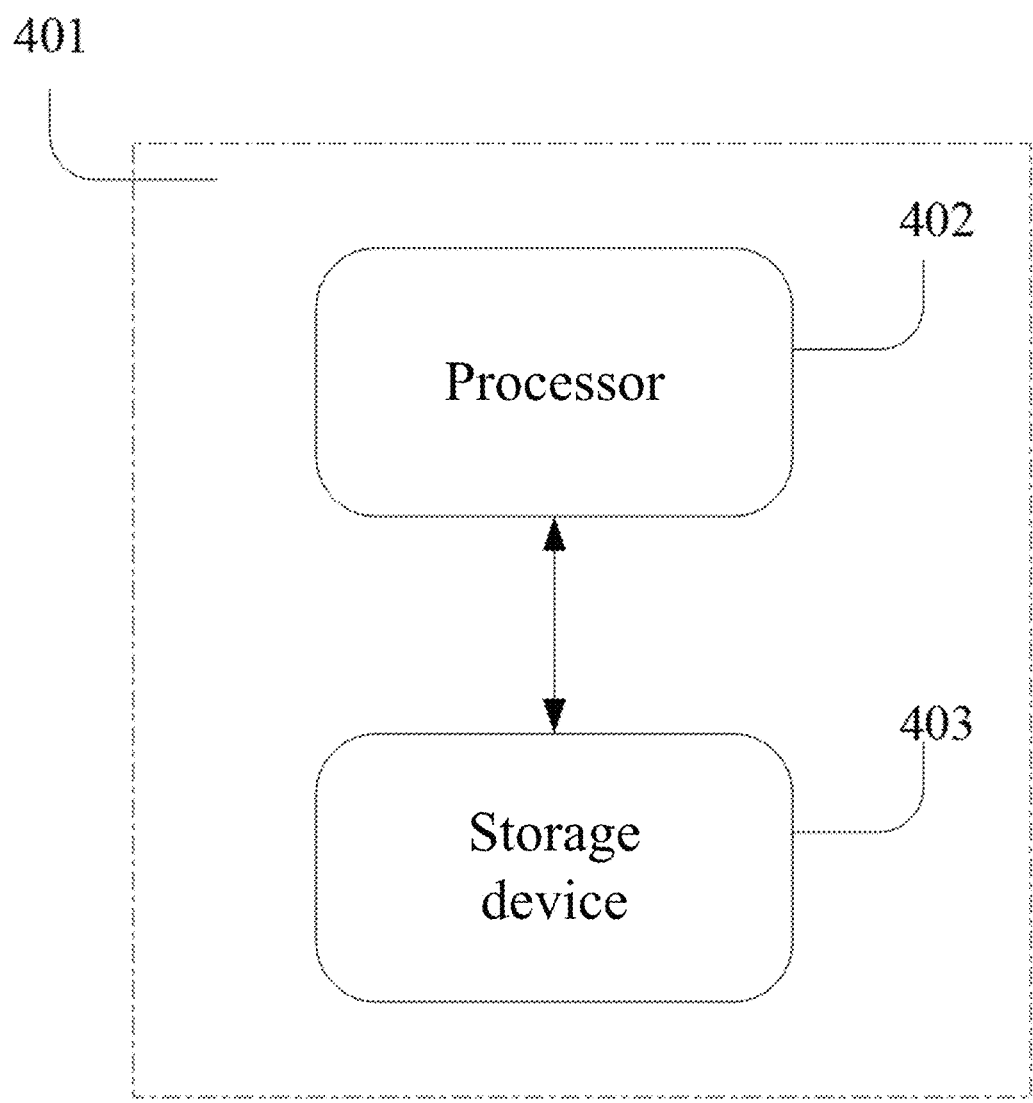
FIG. 10 is a schematic working diagram of a hardware device according to an embodiment of the present disclosure.

Referring to FIG. 10, FIG. 10 is a schematic working diagram of a hardware device according to an embodiment of the present disclosure. The hardware device specifically includes a device 401 for determining a reasonable sampling interval with 3D laser scanning, a processor 402 and a storage medium 403.

Device 401 for determining a reasonable sampling interval with 3D laser scanning: The device 401 for determining a reasonable sampling interval with 3D laser scanning is configured to realize the method for determining a reasonable sampling interval with 3D laser scanning.

Processor 402: The processor 402 is configured to load and execute an instruction and data in the storage medium 403 to realize the method for determining a reasonable sampling interval with 3D laser scanning.

Storage medium 403: The storage medium 403 stores an instruction and data. The storage medium 403 is configured to realize the method for determining a reasonable sampling interval with 3D laser scanning.

In conclusion, the present disclosure has the following beneficial effects: Based on the reversely calculated JRC for the rock joints, the present disclosure determines the reasonable sampling interval for the point cloud data in the 3D laser scanning, and provides a general form of the fitting equation for determining the sampling interval. This reduces an error in roughness evaluation on the rock joints, and further determines, according to a range of the sampling interval, a range of the reasonable sampling interval for the rock joints in the region, thereby facilitating subsequent further applications of the roughness.

The above are merely preferred embodiments of the present disclosure, and are not intended to limit the present disclosure. Any modifications, equivalent replacements, improvements, and the like made within the spirit and principle of the present disclosure shall be all included in the protection scope of the present disclosure.

What is claimed is:

1. A method for determining a reasonable sampling interval with three-dimensional (3D) laser scanning, comprising the following steps:
   step S1, collecting rock joint samples;
   step S2, acquiring point cloud data of the rock joint samples with 3D laser scanning;
   step S3, preprocessing the acquired point cloud data to obtain preprocessed data;
   step S4, conducting indoor mechanical tests on the rock joint samples to determine rock mechanics parameters;
   step S5, calculating, with the preprocessed data, joint roughness coefficients (JRCs) under different intervals obtained from statistical roughness parameters;
   step S6, fitting different relational curves according to a scatter plot between the different intervals and the JRCs to obtain a fitting equation;
   step S7, reversely calculating a JRC of each of the rock joint samples with the rock mechanics parameters to obtain a reversely calculated JRC;
   step S8, substituting the reversely calculated JRC in the step S7 into the fitting equation obtained in the step S6 to determine a reasonable sampling interval for roughness evaluation;
   wherein the rock mechanics parameters comprise a normal stress $\sigma$, a peak shear strength $\tau_p$, a basic frictional angle $\varphi_b$, and a joint compressive strength (JCS);
   wherein the step S5 specifically comprises:
   step S51, evaluating roughness of any two-dimensional (2D) profile of the rock joint samples with a roughness parameter $SD_i$, wherein an interval between selected 2D profiles is the same as a sampling interval of a point cloud for the rock joint samples, and the roughness parameter is calculated by:

$$SD_i = \tan^{-1}\sqrt{\frac{1}{L}\sum_{j=1}^{N-1}\left(\frac{z_{j+1} - z_j}{y_{j+1} - y_j} - \tan i_{ave}\right)^2 (y_{j+1} - y_j)}$$

$$i_{ave} = \tan^{-1}\left(\frac{1}{L}\sum_{j=1}^{N-1}|z_{j+1} - z_j|\right)$$

wherein $z_{j+1}$ and $z_j$ are respectively a Z-coordinate of a (j+1)th point and a Z-coordinate of a jth point in a given 2D profile, $y_{j+1}$ and $y_j$ are respectively a Y-coordinate of the (j+1)th point and a Y-coordinate of the jth point, N is a total number of points in the any 2D profile of the rock joint samples, L is a profile length, and $i_{ave}$ is an average dip angle;
step S52, calculating a $JRC^{2D}$ of a single 2D profile according to the roughness parameter $SD_i$;
step S53, averaging JRCs of all 2D profiles of a given rock joint sample to determine a $JRC^{3D}$ of a rock joint surface:

$$JRC^{2D} = 1.14SD_i - 3.88 \quad JRC^{2D} = 1.14SD_i - 3.88$$

$$JRC^{2D} = 1.14SD_i - 3.88$$

$$JRC^{3D} = \frac{1}{M}\sum_{k=1}^{M} JRC_k^{2D}$$

wherein, M is a total number of the 2D profiles of the given rock joint sample, and i is an ith 2D profile;
step S54, drawing the scatter plot between sampling intervals and the JRCs;
wherein the step S6 specifically comprises:
step S61, constructing the relational curves between the sampling intervals and the JRCs, comprising a first exponential type, a second exponential type and a Logistic type;
step S62, observing each of the relational curves, proceeding with a step S63 when the relational curve is the first exponential type, proceeding with a step S64 when the relational curve is the second exponential type, and proceeding with a step S65 when the relational curve is the Logistic type;

step S63, defining the fitting equation as $y=A_1 \times e^{-x/t_1}+y_0$ or a second-order form $y=A_1 \times e^{(-x/t_1)}+A_2 \times e^{(-x/t_2)}+y_0$, wherein, $A_1$ is an attenuation coefficient, and controls a rate and a direction in attenuation or growth, $t_1$ is a time scale in the attenuation or the growth and is a constant term, $y_0$ is an offset and a constant term, and determines a position of a curve below or above an x-axis;

step S64, performing fitting by:

$$y = \begin{cases} y_0 + A_d + A_g\left(e^{-x_c/t_g} - e^{x/t_g}\right) & x \leq x_c \\ y_0 + A_d e^{-(x-x_c)/t_d} & x > x_c \end{cases}$$

wherein, the two stages of the equation are growth and attenuation, respectively, and $y_0$, $A_d$, $A_g$, $t_g$, $x_c$, and $t_d$ are undetermined coefficients;

step S65, performing fitting by:

$$y = A_2 + (A_1 - A_2)/\left(1 + (x/x_0)^p\right)$$

wherein, $A_1$ is an upper limit of a Logistic function, $A_2$ is a lower limit of the Logistic function, p is a shape parameter, and $x_0$ is a midpoint parameter of the Logistic function;

wherein the reversely calculated JRC in the step S7 is specifically given by:

$$\begin{cases} \tau = \sigma \tan\left[\varphi_b + JRC \lg\left(\dfrac{JCS}{\sigma}\right)\right] \\ JRC = \dfrac{\arctan(\tau/\sigma) - \varphi_b}{\lg(JCS/\sigma)} \end{cases}$$

wherein, τ is the peak shear strength of the rock joint sample obtained in the tests.

2. The method according to claim 1, wherein the preprocessing in the step S3 comprises point cloud data filtering and point cloud data denoising.

3. The method according to claim 1, wherein the indoor mechanical tests in the step S4 comprises a direct shear test, a tilt test and a uniaxial compression test.

4. The method according to claim 1, wherein the first exponential type refers to that a curve rises and then directly approaches to a constant; the second exponential type refers to that a curve rises first and then declines or declines first and then rises, eventually approaching to a constant; and the Logistic type refers to that a curve declines and then directly approaches to a constant.

* * * * *